United States Patent
Eberhart et al.

(10) Patent No.: US 9,022,996 B2
(45) Date of Patent: *May 5, 2015

(54) INSULIN PUMP AND METHOD FOR CONTROLLING A USER INTERFACE OF AN INSULIN PUMP

(71) Applicant: Roche Diagnostics International AG, Rotkreuz (CH)

(72) Inventors: Andreas Eberhart, Inwil (CH); Michael Krieftewirth, Ersingen (CH); Marcel Both, Kirchlindach (CH)

(73) Assignee: Roche Diagnostics International AG, Rotkreuz (CH)

( * ) Notice: Subject to any disclaimer, the term of this patent is extended or adjusted under 35 U.S.C. 154(b) by 37 days.

This patent is subject to a terminal disclaimer.

(21) Appl. No.: 13/679,448

(22) Filed: Nov. 16, 2012

(65) Prior Publication Data

US 2013/0079709 A1    Mar. 28, 2013

Related U.S. Application Data

(63) Continuation of application No. 12/494,479, filed on Jun. 30, 2009, now Pat. No. 8,337,469.

(30) Foreign Application Priority Data

Jul. 1, 2008 (EP) ..................... 08405166

(51) Int. Cl.
| | |
|---|---|
| *A61M 5/00* | (2006.01) |
| *A61M 37/00* | (2006.01) |
| *A61M 5/142* | (2006.01) |
| *A61M 5/172* | (2006.01) |
| *G06F 19/00* | (2011.01) |

(52) U.S. Cl.
CPC ......... *A61M 5/14244* (2013.01); *A61M 5/1723* (2013.01); *G06F 19/3468* (2013.01); *A61M 2005/14264* (2013.01)

(58) Field of Classification Search
CPC ..................... A61M 5/14244; A61M 5/14248; A61M 2005/14264
USPC ....................... 604/65–67, 246–256, 151–155
See application file for complete search history.

(56) References Cited

U.S. PATENT DOCUMENTS

| | | | |
|---|---|---|---|
| 4,731,051 A | 3/1988 | Fischell | |
| 8,337,469 B2 * | 12/2012 | Eberhart et al. | ............... 604/246 |

(Continued)

OTHER PUBLICATIONS

Snodgrass, Ronald D., The Fundamentals of Smart Pump Technology, Biomedical Instrumentation & Technology, vol. 39, No. 6, Nov. 2005, pp. 444-446.

*Primary Examiner* — Nicholas Lucchesi
*Assistant Examiner* — Leah Stohr
(74) *Attorney, Agent, or Firm* — Dinsmore & Shohl LLP

(57) ABSTRACT

An insulin pump comprises a pump device, a control for the pump device, a memory, an operating element for operating the insulin pump and a method for controlling a user interface of the insulin pump are disclosed. The control is designed and programmed such that options for the user of the insulin pump are displayed by the user interface as a function of a user-specific preference profile stored in the memory and as a function of a current time and are provided for selection by using the operating element. The insulin pump can be designed in an auto-adaptive fashion, such that the control continuously updates the user-specific preference profile based on analyzing operating inputs of the user. Embodiments of the invention allow a large range of functions and simple operation, even in the case of miniaturized pumps.

19 Claims, 3 Drawing Sheets

(56) References Cited

U.S. PATENT DOCUMENTS

| | | |
|---|---|---|
| 2003/0212379 A1* | 11/2003 | Bylund et al. ............... 604/504 |
| 2006/0062838 A1* | 3/2006 | DiPierro et al. ............. 424/449 |
| 2007/0118405 A1 | 5/2007 | Campbell et al. |
| 2007/0179434 A1 | 8/2007 | Weinert et al. |
| 2008/0033402 A1 | 2/2008 | Blomquist |
| 2008/0139907 A1 | 6/2008 | Rao et al. |
| 2009/0275886 A1* | 11/2009 | Blomquist et al. ............ 604/66 |

* cited by examiner

INSULIN PUMP AND METHOD FOR CONTROLLING A USER INTERFACE OF AN INSULIN PUMP

CROSS REFERENCE TO RELATED APPLICATIONS

This application is a continuation of currently pending U.S. application Ser. No. 12/494,479 filed Jun. 30, 2009 which claims priority to EP 08405166.3 filed Jul. 1, 2008.

TECHNICAL FIELD

Embodiments of the present invention relate generally infusion systems, and in particular embodiments to an insulin pump comprising a pump device, a control for the pump device, a memory and at least one operating element for the user of the insulin pump to operate the insulin pump, and to a method for controlling a user interface of such an insulin pump.

BACKGROUND

The practice of using insulin pumps in insulin therapy (e.g. for type 1 diabetes) has been known for some time. Insulin pump therapy makes it possible to continuously administer a (variable) basal rate of insulin and also individual boluses, which are used in conjunction with meals and to correct excessively high glucose values in the blood of the patient. As a result of continuously administering the basal rate in accordance with a user-specific basal rate profile, a more equal blood sugar level is attained and thus the organism of the patient is strained less.

Accordingly, infusion systems are known which comprise an infusion pump for insulin (insulin pump) and possibly a blood sugar measurement unit designed as a remote control. In general, the insulin pump should be designed to be as compact as possible so that it is not noticeable and the user finds it comfortable to wear. Thus, the pump comprises a small pump housing which holds a battery, a motor with drive, control and communication electronics and an ampoule fixedly connected to the infusion tube. On its outside, the pump has operating buttons and usually a display as well. This display and the size and number of operating buttons as well are limited by the aspired configuration.

Hence, only limited amounts of information can be displayed on the pump itself. Conventional displays can either output measured blood sugar values and suggested action (bolus, eat), or the menu of the insulin pump. Current insulin pump systems are designed with a fixed operating concept. While operations for a few basic functions (such as administering boluses) can be effected on the insulin pump itself, other functions can only be controlled by the remote control, i.e. the diverse operating functions of the insulin pump are mainly transferred to the remote control.

Even insulin pumps that do not have a remote control, and are thus controlled by operating elements on the pump, have a complex control as a result of the demanded miniaturization.

Hence, complete or comfortable control of current infusion systems for insulin can only be effected with the aid of a remote control. If it is not available, or if all operating elements are realized on the pump, the user has to do without some functions and/or accept more complicated operation. Due to the fact that some functions should always be implemented on the pump for safety reasons, the corresponding display and operating elements cannot be made any smaller in the context of known user interfaces and this puts a limit on the miniaturization of the insulin pumps.

SUMMARY

It is against the above background, that in one embodiment an insulin pump for a user is disclosed. The insulin pump comprises a pump device; a control for the pump device; a memory; and at least one operating element for the user of the insulin pump to operate the insulin pump, wherein the control is designed and programmed such that options are provided to the user of the insulin pump as a function of a user-specific preference profile stored in the memory and a current time.

In another embodiment, the control is designed and programmed such that the options are provided to the user of the insulin pump on the display as a function of and in a certain order in accordance with the user-specific preference profile stored in the memory and the current time.

In still another embodiment, a method for controlling a user interface of an insulin pump is disclosed. The method comprises providing options for the insulin pump as a function of a user-specific preference profile; and storing in a memory of the insulin pump the user-specific preference profile containing said options and a current time.

Further advantageous embodiments and combinations of features of the invention result from the following detailed description and the totality of the patent claims.

BRIEF DESCRIPTION OF THE DRAWINGS

In the figures, identical parts are in principle provided with the same reference symbols. In the drawings used to explain the exemplary embodiment.

DETAILED DESCRIPTION

Figure 1:
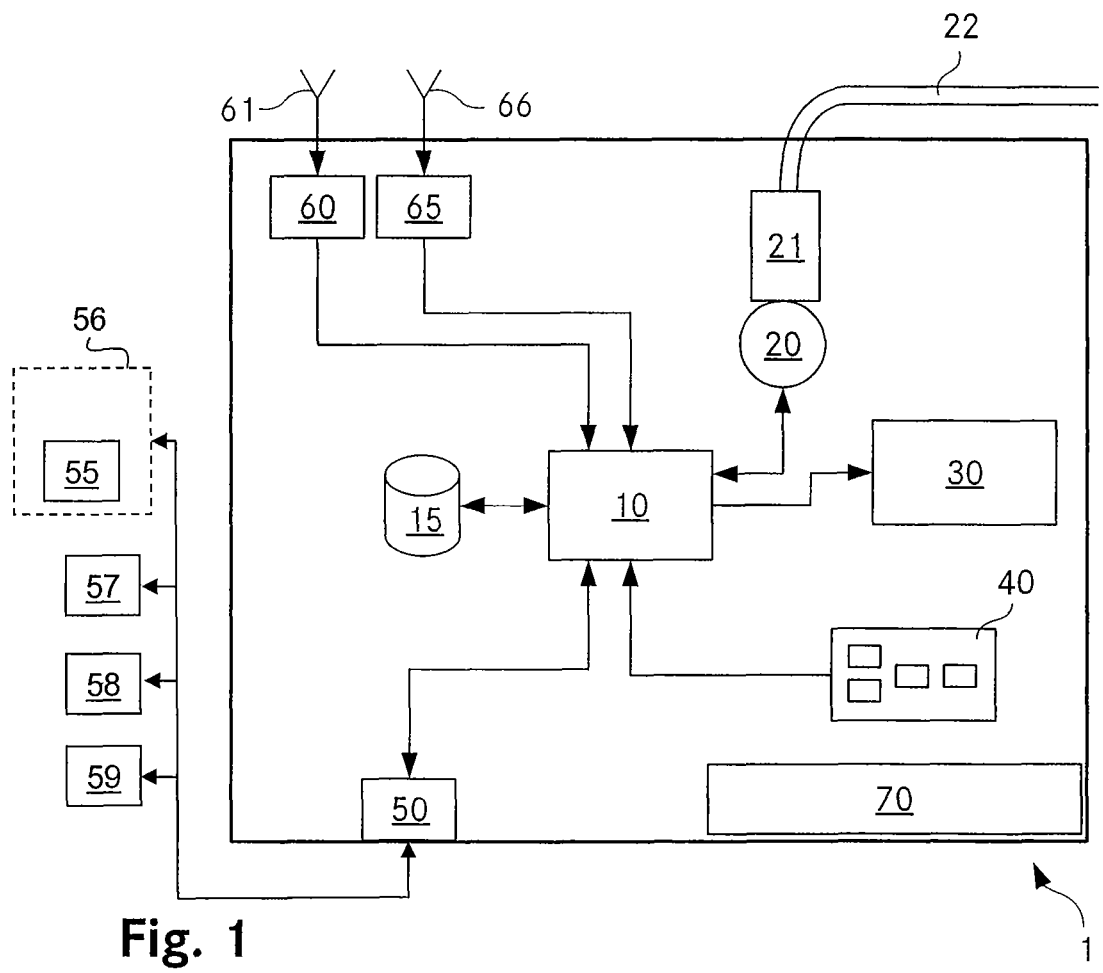
FIG. 1 shows a schematic block diagram of an insulin pump according to the invention.

Certain embodiments of the invention relate to an insulin pump comprising a pump device, a control for the pump device, a memory and at least one operating element for the user of the insulin pump to operate the insulin pump, and other embodiments to a method for controlling a user interface of such an insulin pump which allows a large range of functions and simple operation, even in the case of miniaturized insulin pumps (e.g., insulin pumps with dimensions of less than 106×56×22 mm).

In accordance with an embodiment of the invention, options (i.e., different types of commands, such as e.g., delivery of drug bolus, temporary modification of basal rate, indication of remaining (residual) amount of insulin, etc.) are provided as a function of a user-specific preference profile stored in the memory of the insulin pump and as a function of a current time to the user of the insulin pump for selection by using the operating elements of the insulin pump. In one embodiment, the options are provided on a user-specific basis in the context of the user interface. The user-specific preference profile specifies which functions are preferably selected by the respective user as a function of time, or which functions should be provided for selection by the user at a specific time (for example because these should be selected within the scope of an optimized therapy). Hence, users can quickly and simply reach the functions important to them, even if, in principle, a large number of options are provided. The amount of information to be displayed (e.g. the number of options) can at the same time be reduced, as a result of which a clearer overview is provided and the spatial requirements are reduced.

Hence, in one embodiment, a remotely controlled insulin pump can be designed to be very small (e.g., dimensions of less than 82×56×21 mm) and if no remote control is present, still be operated by means of minimal functions, which can be attained quickly and which are displayed as large as possible on an included display device. Likewise, in the case of systems without a remote control, all functions can be comfortably operated despite the limited space for operating elements and the display device.

In other embodiments, the options are restricted to a certain subset resulting from the preference profile and the current time. This can be effected to the extent that, for example, only a single function can be initiated by pressing a predetermined button, with the function being assigned on the basis of the preference profile and hence it being possible for said function to be replaced in time.

However, in another embodiment, if the insulin pump comprises a display device, it is also possible for options for the user to be displayed on the display device, and be provided for selection with the aid of the at least one operating element, as a function of the user-specific preference profile and the current time. The display on the display device and the selectable menu items are thus generated as a function of the current time and the preference profile stored in the memory. For example, in one embodiment, the display can be preset to "bolus quantity" at the time of the regular bolus administration; at the time of regular decrease in the basal rate (e.g. due to regular sportive activities), the temporary basal rate menu and the corresponding display are activated; and in the rest phase of the user or at the time of an alarm, the time or alarm time is active. Accordingly, user preferred submenus are displayed as a function of the mentioned parameters along with, optionally, the option to return to the "standard menu" in order to be able to access the full functionality at any time if necessary.

As mentioned previously and according to an embodiment of the invention, the insulin pump in addition to a base unit can also comprise a remote control to control the base unit. In one embodiment, the remote control can be integrated in a blood sugar measurement unit. In another embodiment, the at least one operating element for selecting the options provided due to the preference profile can be arranged on the remote control and/or on the base unit. In one embodiment, if the operating element is arranged on the base unit, it is to be appreciated that the user need not necessarily always carry the remote control because, due to such an arrangement, it is also possible to comfortably use the functions important to the user directly on the base unit.

In addition to selecting the information to be displayed and the selection to be provided, in another embodiment it is also possible to output options of a selection menu in a certain order in accordance with the user-specific preference profile, i.e. the most likely selection as a function of the current time and the preference profile is displayed in a prioritized fashion, and the further options follow in order of the selection probabilities assigned thereto. By way of example, in this context "prioritized" means that it is easiest and quickest to select the corresponding option. The prioritized option can for example be selected by simply pressing a confirmation button, while selecting a further option firstly requires moving a cursor onto it.

Advantageously, in one embodiment the preference profile comprises a number of time levels which correspond to different intervals. This is because many physical states and activities of a user generally repeat in certain cycles with different cycle times. Thus, Table 1 lists the following levels, for example, that are feasible within the scope of a method for controlling the user interface according to an embodiment of the invention.

TABLE 1

| infradian | annually | public holidays |
|---|---|---|
|  | semiannually | change of therapy after visit to medical practitioner |
|  | quarterly | change of therapy after visit to medical practitioner |
|  |  | seasons |
|  | weekly | workdays/days off |
|  |  | physical activity |
| circadian | daily | sleeping-waking rhythm |
|  |  | temporary basal rates |
| ultradian | ultradian rhythm (6 h) | dawn - midday - evening - night |
|  | meals | pre-postprandial bolus application |

In still another embodiment, it is possible to additionally acquire and take account of further user-specific habits at each level. In yet another embodiment, in addition to periodic information, it is also possible to integrate individual events into the preference profile in advance, e.g. holidays, hospital stays, irregular physical activities, etc.

In one embodiment, the preference profile can comprise equipment-specific and system-specific information. Here, the equipment-specific information specifically relates to the insulin pump and the system-specific information relates to the user-tailored therapy in general. By way of example, the equipment-specific information can be calibration parameters or measurement intervals; system-specific information, for example, relates to glucose values, e.g. the fasting glucose level, basal rates, typical bolus quantities of the user, etc. It is possible to transfer at least the system-specific information to other equipment via an interface and/or it is possible for other equipment to receive said system-specific information. This makes it possible to supply a plurality of equipment, used within the scope of a therapy for different purposes, with the same system-specific information while the equipment-specific information differs depending on the equipment. System-specific information can be interchanged automatically, for example by means of a wireless connection. In still another embodiment, a saved preference profile can be exported in order to save it or transfer it to other equipment, for example a replacement insulin pump.

Advantageously and in another embodiment, the preference profile comprises information about at least one most frequently used command, this information being updated on a regular basis (e.g. daily, weekly, or monthly). This at least one most frequently used command can be retrieved directly via a special function with the aid of the operating elements. For example, this command can be assigned its own button or a fixed spot in every selection menu. The most frequently used command can be replaced as a function of the current time and possibly further information (e.g. relating to the current state or current activity of the user), or it can always be the same command independent of the time, in which case a change is undertaken only if another command is used more frequently overall.

In one preferred embodiment, a database is stored in the memory and comprises location-specific peculiarities relevant to insulin therapy and the preference profile is adapted as a function of a current location of the user based on the database. By way of example, the database can comprise information relating to country-specific meal or rest times and eating customs (for example, information relating to late night eating or rest time around midday in more southerly countries). The country-specific or location-specific information can also be linked to information relating to the customs of the user: for example, if the user owns a holiday home, the rhythm of life will be different there than at the place of work or residence. If the insulin pump determines that the user is at this holiday home, or if this information is transferred to said pump or input, this is taken into account in a correspondingly adapted preference profile.

Accordingly, the insulin pump in another preferred embodiment comprises means for determining a location, in particular a receiver for a navigation system or an interface to such a receiver. This ensures that the control of the insulin pump is always informed with regard to the location of the user and can take the country-specific or location-specific information into account for the user-specific control of the user interface.

Alternatively, the location is specified by the user, e.g. with the aid of the operating elements of the insulin pump.

Advantageously and in one embodiment, the insulin pump is designed in an auto-adaptive fashion, with the control continuously updating the user-specific preference profile based on analyzing operating inputs of the user. For example, the control correlates the inputs of the user with the respective time and the respective date, and possibly with further available data. Statistical analysis can be used in a further step to obtain the preference profile from the linked data. The profile can be updated continuously or after certain intervals (e.g. daily or weekly). In the process of updating, more recent inputs are preferably weighted more strongly than older inputs, with it being possible for the weighting to be selected differently depending on the timeframe of the analysis. Even if the preference profile is based on the usage of the functions by the user, certain (e.g. safety-relevant) functions can be fixedly assigned a predetermined weighting so that they can always be called in a simple manner.

Alternatively or in addition, the user-specific preference profile is generated based on analyzing operating inputs of the user during one or more learning intervals. Thus it is possible, for example, to provide a learning interval with duration of a few weeks when the insulin pump is first used. It is possible for further learning intervals to follow if there is a significant change in the rhythm of life of the user.

Alternatively, or in order to obtain a first, provisional preference profile, it is possible to question the user and/or undertake user analysis when the insulin pump is being set up or within the context of schooling. This information is subsequently entered with the aid of the operating elements of the insulin pump or—preferably—via external equipment connected to the insulin pump. The infusion system according to another embodiment of the invention can provide a user interface on some equipment (the insulin pump, a remote control or on further equipment such as a PC or a PDA), by means of which the preference profile can be adapted in a user-controlled manner and/or which makes it possible to manage a multiplicity of preference profiles.

Alternatively, or in addition to the evaluation of the user inputs, it is possible for the control to take into account data of a sensor provided for monitoring the user when generating or updating the user-specific preference profile. Suitable data comprises physiological data such as pulse, blood pressure, body temperature or blood sugar levels; information regarding activities of the user such as movement, acceleration, outside temperature, etc.; or information regarding the location of the user (see above). Such data can also be taken into account when displaying and providing the options.

The insulin pump according to another embodiment of invention can also comprise an interface to a digital scheduler, it being possible for this scheduler to be implemented on a PDA, a mobile telephone, a notebook, a desktop PC or another platform. Such schedulers usually have information relevant to the insulin therapy stored in them, for example holidays or days off, and information regarding activities such as sport. If this information is made available to the insulin pump, the user interface can be controlled in a manner which is even more specific in terms of the needs of the user.

In one embodiment, the control is designed and programmed such that if the user makes a selection which deviates from the user-specific preference profile, a confirmation prompt is output before carrying out the selection (e.g. by outputting "Are you sure?" with the prompt to confirm this selection once again). This makes it possible to increase the safety of the infusion system according to the invention in a simple manner. The confirmation prompt can be limited to safety-relevant inputs, e.g. to administering a bolus, changing the basal rate, etc., whereas further inputs (e.g. selecting a display setting or only outputting information) are accepted and carried out without further enquiry.

Advantageously and in one embodiment, the insulin pump comprises a receiver for a time signal or an interface to such a receiver. Corresponding time signals are available in a number of regions, for example the time signal DCF77, which can be received in western and central Europe, or time signals from a mobile radio network. This ensures that the insulin pump always has available the current local time and injects the appropriate correct basal rate. Moreover, a change in the time zone can be recognized automatically and can be taken into account when evaluating the preference profile.

Furthermore, the insulin pump in still another embodiment comprises a wireless communication interface. This enables a simple control of the pump, for example by using a remote control; simple updating of the pump parameters and the preference profile; and a simple readout of the information saved in the pump.

Readout of the currently saved preference profile is expedient because the preference profile supplies characteristic information about the user's handling of the therapy. The HCP (healthcare provider) of the user can provide assistance in optimizing the therapy or the user's handling of the therapy on the basis of the read-out profile.

Implementation Examples

FIG. 1 shows a schematic block diagram of an insulin pump according to an illustrative embodiment of the invention. The insulin pump 1 comprises a central control 10, implemented by a microprocessor. This control 10 can store data to memory 15, or retrieve it therefrom. The central control 10 controls a pump 20 which comprises a motor and a drive and feeds insulin from an ampoule 21 into an infusion tube 22 of an infusion set according to the requirements of the user. Furthermore, the insulin pump 1 has a display 30 which can be read from the outside and operating buttons 40 which are respectively connected to the control 10 for outputting or inputting information. Furthermore, the illustrated insulin pump 1 also has a communication module 50 which is also connected to the central control 10 and which has wireless and wired interfaces for communication with further equipment, e.g., with a remote control 55 (which in one embodiment can be designed as part of a blood sugar measurement unit 56), with a digital scheduler (e.g. a PDA) 57, a personal computer 58, a sensor 59 for providing data (e.g., physiological data such as pulse, blood pressure, body temperature or blood sugar levels; information regarding activities of the user such as movement, acceleration, outside temperature, etc.) and/or a further insulin pump.

Figure 2A:
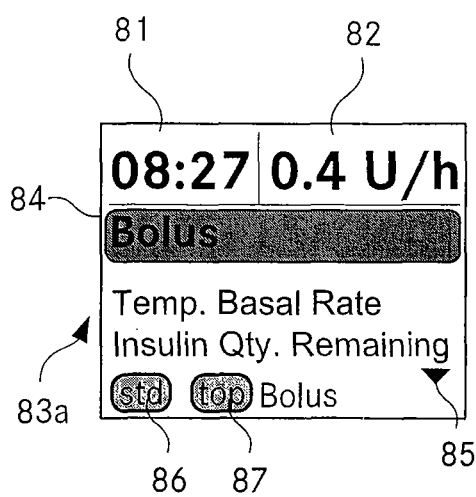
FIGS. 2A and 2B show exemplary outputs or graphical user interfaces that can be provided on a display of an insulin pump according to a user specified preference profile.
Figure 2B:
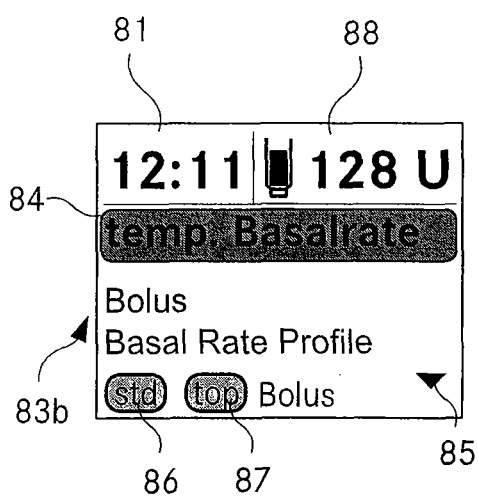

Additionally, in the illustrated embodiment the insulin pump 1 comprises a receiver 60 for a navigation system with a corresponding antenna 61 for information regarding the location of the user, and a receiver 65 for a time signal with a corresponding antenna 66, the receivers 60, 65 in turn being connected to the central control 10. An integrated battery 70 supplies electricity to the individual components of the insulin pump 1. In memory 15, a preference profile 80 is stored and accessible by the central control 10 for use in arranging the user specified options on the display 30. Reference is made hereafter also to FIGS. 2A and 2B.

FIGS. 2A and 2B show two exemplary outputs or graphical user interfaces which can be provided on the display 30 of the insulin pump 1 according to the preference profile 80. The first graphical user interface illustrated in FIG. 2A comprises information about the current time 81, the current insulin delivery rate 82 in units per hour as well as a menu selection 83a with three menu items: bolus, temp. basal rate, and insulin quantity remaining (which indicates the residual amount of insulin). A pointer 84 which is pointing at the first displayed menu item ("Bolus") and an arrow-like display 85 which highlights the fact that further menu items are available.

The preference profile 80 of the user decides—as explained in more detail below—what information is displayed (time 81, insulin delivery rate 82), what options, e.g. "Bolus", "temp. Basal rate", and "Insulin Quantity Remaining" (which will indicate the residual amount of insulin), are available in the menu selection 83a and in what order they are displayed. The pointer 84 in each case points at the first displayed menu item so that said menu item can be selected by simply pressing one of the operating buttons 40, e.g., a "confirm" button. First and second display icons 86, 87 are also provided in the graphical user interface embodiment. The first display icon 86 ("std") highlights the fact that by pressing an appropriately marked button, it is possible to switch to a standard menu structure of the insulin pump which does not change with time and by means of which all available functions can be called. The second display icon 87 ("top") highlights the fact that, by pressing an appropriately marked button, it is possible to select the command most used by the user ("Bolus" in this case).

FIG. 2B illustrates a second graphical user interface that can be displayed at a different point in time. It in turn shows the time 81, but in this case also the amount of insulin remaining in the ampoule (residual amount of insulin 88) in units. Furthermore, the second graphical user interface also comprises a menu selection 83b, but this now has in part different menu items and different ordering: temp. basal rate, bolus, and basal rate profile. The pointer 84 again points at the first displayed menu item ("temp. Basal rate") and an arrow-like display 85, which highlights the fact that further menu items are available, is again present, as are display icons 86, 87 which highlight the fact that a standard menu structure and a direct call of the most used function are available.

Figures 3A, 3B:
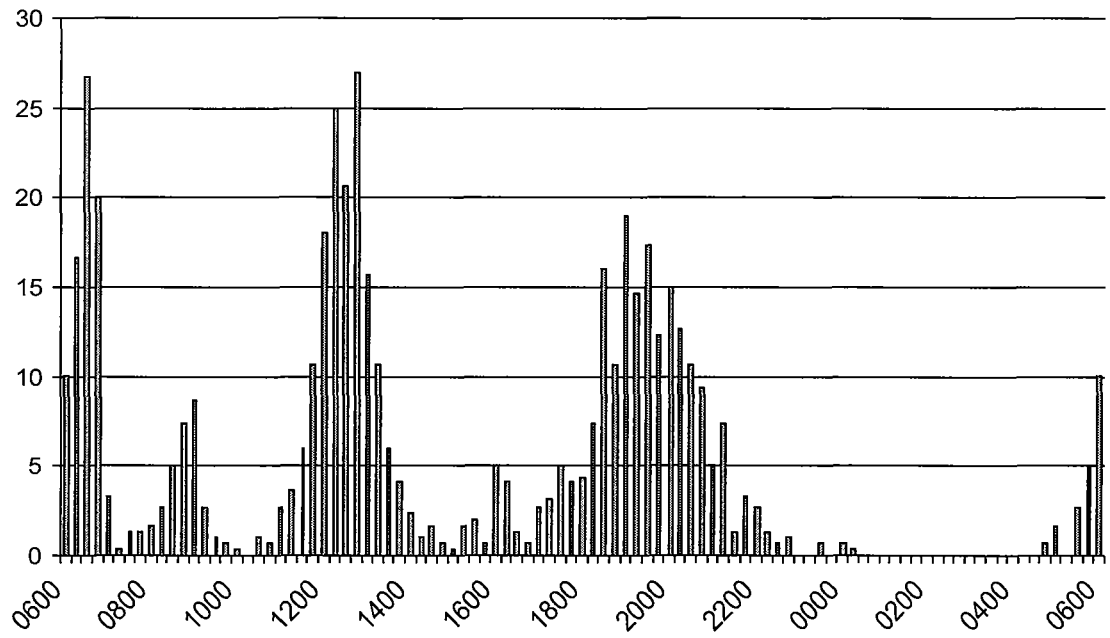
FIGS. 3A, 3B and 3C show histograms regarding the usage of different functions of the insulin pump during the day.
Figure 3C:
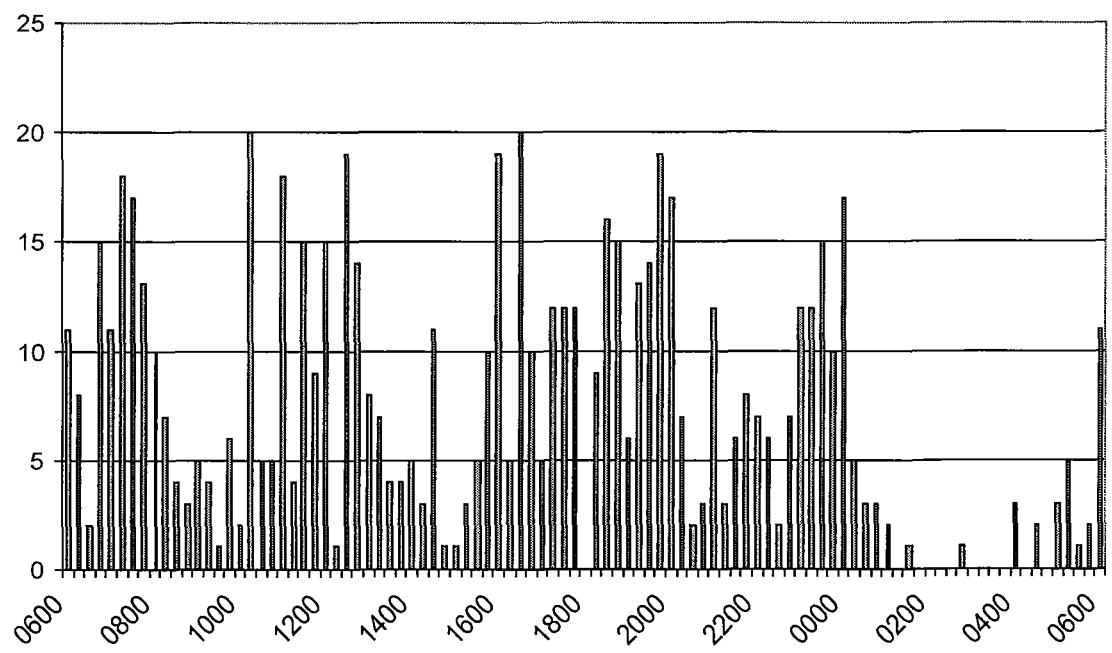

FIGS. 3A-3C show histograms relating to the usage of three different functions of the insulin pump throughout the day (from 6 am to 6 am the next day); with the actions of the user being acquired over a relatively long period of time (e.g. 3 months) and illustrated in these diagrams.

FIG. 3A shows the usage distribution of a function which has clear maximums, specifically at approximately 7 am, at approximately 9 am, between 12:30 pm and 1:30 pm and between 7 pm and 9 pm. Hence, this is a function (e.g. administering a bolus) which the user calls regularly at certain times, but hardly ever outside said times.

FIG. 3B shows the usage distribution of a further function which has certain maximums and minimums, particularly in the early afternoon, in the late afternoon and after 8 pm. However, in contrast to the distribution of the first function in accordance with FIG. 3A, the maximums are not as clear and this function is also regularly called between said maximums, at least during the day. By way of example, a corresponding distribution results from a function such as the "temporary basal rate change".

FIG. 3C shows a histogram of a further function. In this case, no clear trend can be recognized with the exception of the low call frequency during the night-time hours.

Corresponding usage data is automatically gathered by the insulin pump according to an embodiment of the invention for all functions available on the insulin pump, including the set outputs on the display, and said usage data is linked to further information (e.g. day of the week, season, location of the user, pulse, possibly information made available by the scheduler, etc.) in addition to the temporal information. This makes it possible to subsequently itemize the usage frequency in accordance with the mentioned criteria in another embodiment.

The following are typical commands for an insulin pump, the usage frequency of which can be determined: select basal rate profile; display bolus memory; initiate bolus (standard, delayed); temporary basal rate change (increase/decrease); start and stop dispensing insulin; enter bolus increment; set time/time zone; and program basal rate profile.

In one embodiment, display functions, the frequency of which is likewise acquired, include: current basal rate (as a function of the profile) in U/h; residual amount of insulin in U; time/date; error messages/alarms; battery level; settings, menus, submenus; operating state (STOP/RUN); previous boluses (time, date, amount); and daily amounts. In other embodiments additional display functions may be provided as such becomes desired.

In one embodiment, the user-specific preference profile results from the above mentioned usage frequency analyses. Table 2 below shows a simplified section of an exemplary preference profile, the itemization only being undertaken according to time (half-hourly sections) and workday/day off for reasons of simplicity and in which only five commands/display functions are illustrated. The numbers specified represent the respective preference value of the function in the given interval and the given day of the week (in arbitrary units), with the respectively highest value being boxed-in.

TABLE 2

|  |  | Opt1 | Opt2 | Opt3 | Opt4 | Opt5 |
|---|---|---|---|---|---|---|
| 0600 | Mon-Fri | 24 | 4 | 11 | 6 | 8 |
|  | Sat/Sun | 8 | 4 | 8 | 4 | 8 |
| 0630 | Mon-Fri | 32 | 3 | 13 | 4 | 7 |
|  | Sat/Sun | 9 | 2 | 9 | 3 | 7 |
| 0700 | Mon-Fri | 25 | 5 | 22 | 5 | 9 |
|  | Sat/Sun | 10 | 5 | 8 | 4 | 9 |
| 0730 | Mon-Fri | 21 | 7 | 17 | 7 | 12 |
|  | Sat/Sun | 12 | 4 | 11 | 5 | 12 |
| 0800 | Mon-Fri | 14 | 24 | 12 | 3 | 11 |
|  | Sat/Sun | 19 | 14 | 12 | 1 | 11 |
| 0830 | Mon-Fri | 10 | 11 | 8 | 10 | 9 |
|  | Sat/Sun | 22 | 11 | 14 | 3 | 9 |
| 0900 | Mon-Fri | 11 | 7 | 13 | 8 | 8 |
|  | Sat/Sun | 24 | 12 | 15 | 6 | 8 |
| 0930 | Mon-Fri | 8 | 5 | 12 | 11 | 3 |
|  | Sat/Sun | 18 | 14 | 10 | 7 | 3 |
| 1000 | Mon-Fri | 7 | 11 | 13 | 14 | 2 |
|  | Sat/Sun | 14 | 16 | 8 | 10 | 2 |
| 1030 | Mon-Fri | 7 | 8 | 13 | 12 | 1 |
|  | Sat/Sun | 5 | 14 | 11 | 14 | 1 |
| 1100 | Mon-Fri | 12 | 14 | 11 | 8 | 0 |
|  | Sat/Sun | 8 | 14 | 14 | 15 | 0 |
| 1130 | Mon-Fri | 18 | 15 | 12 | 4 | 0 |
|  | Sat/Sun | 14 | 12 | 10 | 11 | 0 |
| 1200 | Mon-Fri | 26 | 22 | 13 | 6 | 1 |
|  | Sat/Sun | 12 | 14 | 7 | 9 | 1 |
| 1230 | Mon-Fri | 29 | 18 | 8 | 5 | 0 |
|  | Sat/Sun | 13 | 11 | 5 | 6 | 0 |
| 1300 | Mon-Fri | 25 | 10 | 11 | 5 | 2 |
|  | Sat/Sun | 10 | 10 | 9 | 4 | 2 |
| 1330 | Mon-Fri | 21 | 12 | 9 | 4 | 0 |
|  | Sat/Sun | 7 | 14 | 9 | 2 | 0 |
| 1400 | Mon-Fri | 8 | 14 | 13 | 5 | 1 |
|  | Sat/Sun | 8 | 15 | 14 | 7 | 1 |
| 1430 | Mon-Fri | ... | ... | ... | ... | ... |

It can be seen from the table that the usage frequencies are in part quite different on workdays and days off. By way of example, the insulin pump is now controlled such that (as illustrated in FIGS. 2A, 2B) on a Saturday at 8:27 am, the ordering: bolus (Opt 1)/temporary basal rate (Opt 2)/display residual amount of insulin (Opt 3) is effected, whereas at 12:11 pm on the same day, the ordering: temporary basal rate/bolus/basal rate profile (Opt 4) results. The options provided and their ordering are adapted appropriately.

The real implementation does not only distinguish between time of day and workday/day off, but further factors are also considered, as described above. This can be accommodated in other embodiments by the table correspondingly having additional rows for further parameter combinations or by the preference values at a given time being calculated in a known manner from partial preference values. These partial preference values can for example correspond to an ultradian, a circadian and an infradian partial preference, which are summed for the given point in time.

In still other embodiments, if information regarding particular conditions or activities of the user is present (for example, information from the scheduler which indicates that the user plans physical activity shortly after the current point in time), then these conditions can be accommodated within the scope of the method according to the invention; for example, the preference values are taken from a special "sport profile" for a certain interval before and during the physical exertion. Such a profile is then always updated—like the usual preference profile—on the basis of the effected user inputs when said profile is active. Similar specific profiles may be called when further situations are present ("travel", "late food", "holiday", etc.). In the case of a shift worker, it is also feasible that, for example, a "day shift profile" and a "night shift profile" are present. In still other embodiments, a different profile can be selected automatically or manually by the user. It is possible to define a multiplicity of profiles and respectively one of them is in each case selected as the currently selected preference profile. The individual profiles can be generated, read, modified or exported independently of one another.

In one embodiment, if the receiver 65 for the time signal and/or the receiver 60 for the navigation system determine that there is a change in the time zone, the internal time of the insulin pump is automatically changed and there is a corresponding adaptation of the (basal) quantity of insulin to be released and the information and user preferences to be displayed.

In another embodiment, if the user confirms a selection, which does not conform to his preference profile (and thus correspondingly undershoots a predetermined minimum preference value) and which is relevant to the health of the user (that is to say, for example, something which influences the current or future dispensing of insulin), then there is an additional confirmation prompt which the user has to acknowledge before the selected function is carried out.

In still another embodiment, an initial preference profile can be predetermined prior to the first use of the insulin pump. By way of example, a preference profile can already be set up to be user-specific based on questioning of the user or on the basis of information about the user which is already known. In another embodiment, if the user previously used an insulin pump with a preference profile, it is possible to take over the preference profile from the earlier pump. Alternatively, a predetermined general initial profile is saved in the insulin pump. The user-specific preference profile will be set automatically within the scope of daily use due to the auto-adaptive function of the insulin pump.

The initial preference profile can be generated externally and read via the interfaces of the communication module 50. Similarly, analysis, manual adaptation or processing of the preference profile is advantageously undertaken externally (e.g. on a PC) and the changed profile is subsequently read into the pump. The export and import possibilities for the profile also create a simple possibility for making backup copies of the profile and/or the information on which it is based.

The invention is not limited to the illustrated exemplary embodiments; in particular, the insulin pump can have a different design and have additional components or not have elements such as a receiver for a navigation system or for a time signal. The information display and the menu navigation of the insulin pump will also, in general, be designed differently, for example by using a number of graphics elements. If only a small-area display is available, it is possible in each case that only one option is displayed, with it being possible to switch ("scroll") to further options with the aid of an operating element. In this case, the preference profile determines the order in which the options are displayed.

The preference profile can be updated and the preferred functions and displays can be determined in a number of ways—corresponding methods are known. As a variant to the methods described above, in another embodiment it is possible for the preference profile to be generated during a predetermined learning interval on the basis of the operation and selection operations undertaken by the user. Once the learning interval has been completed, it is possible to continue to acquire the operations of the user and put them in relation to the preference profile. If analysis yields that there are often or statistically significant deviations from the preference profile, this can be communicated to the user and the generation of a new preference profile can be proposed.

When generating the preference profile in the learning interval, or during its continuous updating, it is possible that certain non-characteristic times can be blocked or excluded from the statistical analysis for generating or modifying the preference profile.

In conclusion, it should be noted that the embodiments of the invention provide an insulin pump and a method for controlling a user interface of such an insulin pump which allow for a large range of functions and simple operation, even in the case of miniaturized pumps.

What is claimed is:

1. An insulin pump for a user comprising:
   a pump device;
   a control for the pump device;
   a memory; and
   at least one operating element for the user of the insulin pump to operate the insulin pump,
   wherein:
      the control is designed and programmed such that a menu of control functions is provided to the user of the insulin pump based on a user-specific preference profile stored in the memory and a current time, wherein the user-specific preference profile comprises information about at least one most frequently used command, wherein the control updates the information about the at least one most frequently used command on a regular basis, and the at least most frequently used command can be retrieved directly with the aid of the at least one operating element, and
      a database is stored in the memory and comprises location-specific peculiarities relevant to insulin therapy, wherein the user-specific preference profile is adapted as a function of a current location of the user based on the database.

2. The insulin pump according to claim 1 further comprising a display device, the menu of control functions being displayed on the display device based on the user-specific preference profile and the current time and provided for selection by the user using the at least one operating element.

3. The insulin pump according to claim 2, wherein the menu of control functions is displayed in a certain order in accordance with the user-specific preference profile and the current time.

4. The insulin pump according to claim 1, wherein the control continuously updates the user-specific preference profile based on analyzing operating inputs of the user.

5. The insulin pump according to claim 1, wherein the user-specific preference profile is generated based on analyzing operating inputs of the user during one or more learning intervals.

6. The insulin pump according to claim 1 further comprising a sensor for monitoring the user, wherein the control takes data of the sensor into account when generating or updating the user-specific preference profile.

7. The insulin pump according to claim 1, wherein the control is designed and programmed such that if the user makes a selection which deviates from the user-specific preference profile for the current time, a confirmation prompt is output before carrying out the selection.

8. The insulin pump according to claim 1, wherein the user-specific preference profile comprises a number of time levels which correspond to different intervals.

9. The insulin pump according to claim 8, wherein the different intervals comprises infradian, circadian and ultradian intervals.

10. The insulin pump according to claim 1, further comprising a communication module, wherein the insulin pump receives and transfers the user-specific preference profile via the communication module.

11. The insulin pump according to claim 1 further comprising a navigation system receiver.

12. The insulin pump according to claim 10, wherein the communication module comprises a wireless communication interface.

13. The insulin pump according to one of claim 1, wherein the insulin pump comprises a base unit and a remote control for controlling the base unit.

14. The insulin pump according to claim 13, wherein the remote unit is part of a blood sugar measurement unit with a remote control function.

15. The insulin pump according to claim 1, wherein the regular basis is daily, weekly, or monthly.

16. An insulin pump comprising:
   a pump device;
   a control for the pump device;
   a memory;
   a display; and
   at least one operating element for the user of the insulin pump to operate the insulin pump,
   wherein:
      the control is designed and programmed such that a menu of control functions is provided to the user of the insulin pump based on a user-specific preference profile stored in the memory and a current time, wherein the user-specific preference profile comprises information about at least one most frequently used command, wherein the control updates the information about the at least one most frequently used command on a regular basis, and the at least most frequently used command can be retrieved directly with the aid of the at least one operating element, and
      a database is stored in the memory and comprises location-specific peculiarities relevant to insulin therapy, wherein the user-specific preference profile is adapted as a function of a current location of the user based on the database.

17. The insulin pump according to claim 16, wherein the regular basis is daily, weekly, or monthly.

18. A method for controlling a user interface of an insulin pump comprising:
   providing a menu of control functions for the insulin pump based on a user-specific preference profile;
   storing in a memory of the insulin pump the user-specific preference profile containing said menu and a current time, wherein the user-specific preference profile comprises information about at least one most frequently used command, wherein the control updates the information about the at least one most frequently used command on a regular basis, and the at least most frequently used command can be retrieved directly with the aid of an at least one operating element; and
   storing in said memory a database comprising location-specific peculiarities relevant to insulin therapy, wherein the user-specific preference profile is adapted as a function of a current location of the user based on the database.

19. The method for controlling a user interface of an insulin pump according to claim 18, wherein the regular basis is daily, weekly, or monthly.

\* \* \* \* \*